United States Patent [19]

Brennan et al.

[11] Patent Number: 5,218,075

[45] Date of Patent: Jun. 8, 1993

[54] AMIDE AND HYDROXYMETHYL FUNCTIONALIZED POLYETHERS AS THERMOPLASTIC BARRIER RESINS

[75] Inventors: David J. Brennan; Jerry E. White; Anthony P. Haag; Shari L. Kram, all of Midland, Mich.

[73] Assignee: The Dow Chemical Company, Midland, Mich.

[21] Appl. No.: 836,626

[22] Filed: Feb. 13, 1992

Related U.S. Application Data

[62] Division of Ser. No. 520,689, May 8, 1990, Pat. No. 5,115,075.

[51] Int. Cl.$^5$ .................. C08G 59/28; C08G 59/32; C07D 303/12; C07D 303/34
[52] U.S. Cl. .......................... 528/99; 549/553
[58] Field of Search ........................... 528/99; 549/553

[56] References Cited

U.S. PATENT DOCUMENTS

| | | | |
|---|---|---|---|
| 2,602,075 | 7/1952 | Carpenter et al. | 528/95 |
| 3,210,428 | 10/1965 | Guest et al. | 568/640 |
| 3,305,528 | 2/1967 | Wynstra et al. | 528/95 |
| 4,367,328 | 1/1983 | Bertram et al. | 549/553 |
| 4,837,293 | 6/1989 | Silvis et al. | 528/99 |

OTHER PUBLICATIONS

"Selectively in New Beta Adrenergic Blocking Agents". (3-Amino-2-Hydroxypropoxy) Benzamides. Shtacher et al., Chemical Abstract 79(15):87337t (1973).

*Primary Examiner*—Melvyn I. Marquis
*Assistant Examiner*—Frederick Krass

[57] ABSTRACT

Polyethers having improved barrier to oxygen are normally solid, thermoplastic polyethers having aromatic ether repeating units in their backbones and pendent hydroxyl moieties and pendent amido, N-substituted amido and/or hydroxyalkyl moieties. Such polyethers are prepared by reacting diglycidyl ethers of dihydric aromatic compounds such as the diglycidyl ether of bisphenol A with dihydric phenols having pendent amido, N-substituted amido and/or hydroxyalkyl moieties such as 2,2-bis(4-hydroxyphenyl)acetamide and 3,5-dihydroxybenzamide.

2 Claims, No Drawings

AMIDE AND HYDROXYMETHYL FUNCTIONALIZED POLYETHERS AS THERMOPLASTIC BARRIER RESINS

CROSS-REFERENCE TO RELATED APPLICATION

This is a divisional of application Ser. No. 520,689 filed May 8, 1990 now U.S. Pat. No. 5,115,075.

BACKGROUND OF THE INVENTION

This invention relates to thermoplastic polyethers having pendant hydroxyl moieties and to articles prepared from such polyethers.

Hydroxyphenoxyether polymers are known to be useful in the fabrication of articles exhibiting barrier properties. See, for example, Reinking et al, *J. Poly Sci.*, Vol. 7, pp. 2135-2144, pp. 2145-2152 and pp. 2153-2160 (1963) and *Encyclopedia of Polymer Science and Technology*, Vol. 10, pp. 111-122. Such polymers generally have only moderate oxygen barrier, i.e., they generally exhibit oxygen transmission rates of 2 to 75 cm$^3$-mil/100 in$^2$-atm-day.

In view of the limited barrier properties of the prior art polymers having pendant hydroxyl moieties and phenoxyether moieties, it would be highly desirable to provide a polymer having a high barrier (i.e., oxygen transmission rate less than 5 cm$^3$-mil/100 in$^2$-atm-day) to oxygen. Polymers that retain such high barrier in both dry and moist environments would be especially desirable.

SUMMARY OF THE INVENTION

The present invention is, in one aspect, a normally solid, thermoplastic polyether having repeating units represented by the formula:

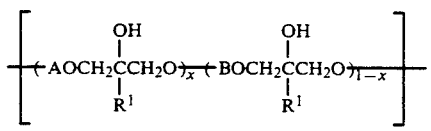

wherein each A is individually a divalent aromatic moiety bearing an amide or hydroxymethyl group; each B is individually a divalent aromatic moiety different from A; R$^1$ is hydrogen or a monovalent hydrocarbon, and x is a number sufficient to reduce the oxygen permeability of the polyether to a value which is measurably lower than that of a polyether consisting of repeating units represented by the formula:

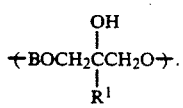

Surprisingly, the presence of the A-component in the polyether of this invention results in a polymer having thermoplastic character and increased barrier to oxygen in both dry and moist environments. The polymer can be extruded, molded or fabricated by other heat plastifying means to form a variety of articles such as films, bags and tubes as well as stand-alone containers. Such polymers retain their thermoplastic character even after being subjected to such heat plastifying conditions. By "normally solid", it is meant that the polymer is solid at ambient temperatures, e.g., 15° C.-35° C.

In a second aspect, this invention is one of the precursors used to prepare the polyether, i.e., a diglydicyl ether of certain amido-dihydric phenols and N-substituted dihydric phenols as hereinafter defined.

In a third aspect, this invention is a novel amido-dihydric phenol, e.g., 2,2-bis(4-hydroxyphenyl)acetamide, which exhibits surprising barrier properties when incorporated into the aforementioned polyether.

In a fourth aspect, this invention is an article suitable for packaging oxygen-sensitive materials such as foodstuffs and medicines wherein the article is fabricated of the polyether. This article can be in the form of a molded container, an impermeable film or a coating or an interlayer of a laminate or a coextruded container.

In addition to their use as barrier containers and films, the polymers of this invention are also useful as molding, extrusion and casting resins.

DETAILED DESCRIPTION OF THE INVENTION

In preferred embodiments, the polyethers are copolyethers having repeating units represented by Formula I, each A is individually represented by one of the formulas:

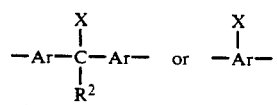

wherein Ar is arylene such as phenylene and naphthalene and X is amido, N-substituted amido such as N-monosubstituted amido and N,N-disubstituted amido and hydroxyalkyl such as hydroxymethyl; each B is individually carbonyldiphenylene, m-phenylene, sulfonyldiphenylene, p-phenylene, isopropylidene diphenylene, biphenylene, biphenylene oxide, methylenediphenylene, biphenylene sulfide, naphthylene, biphenylenecyanomethane, 3,3'-dialkyldiphenylene-isopropylidene, bis(N-phenyleneamido) alkylene, 3,3',4,4'-tetraalkyldiphenylene-isopropylidene, and the corresponding alkyl-substituted derivatives of the other named divalent aromatic moieties; and x is a number from about 0.05 to 1. R$^2$ is hydrogen or a hydrocarbyl or substituted hydrocarbyl wherein hydrocarbyl is a monovalent hydrocarbon such as alkyl, cycloalkyl, aralkyl, or aryl and the substituent(s) is a monovalent moiety which is inert in the reactions used to prepare the copolyether. Examples of such substituents include cyano, halo, amido, hydroxy and hydroxyalkyl. More preferably A is represented by the formulas:

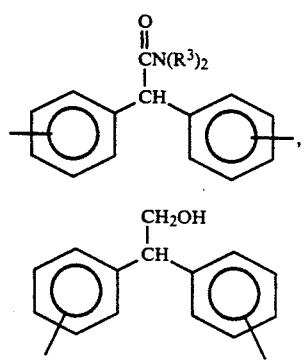

-continued or

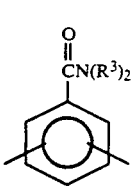

wherein each $R^3$ is individually hydrogen, alkyl having from 1 to 6 carbons or hydroxyalkyl having 2 to 4 carbons; B is isopropylidenediphenylene, biphenylene such as 4,4'-biphenylene and 3,3'-biphenylene, or phenylene such as 1,3-phenylene and 1,4-phenylene; $R^1$ is hydrogen, methyl, ethyl or propyl; and x is about 0.25 to about 1.0. The copolyethers are most preferably those represented by the formula:

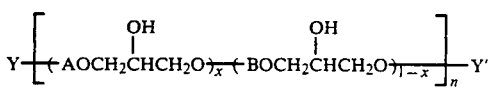

wherein A, B and x are as defined above, Y is predominantly hydroxy and Y' is predominantly

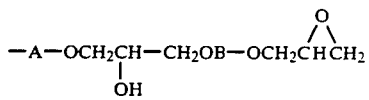

and n is a whole number from 10 to about 1000.

The copolyethers of this invention are suitably prepared by contacting one or more of the diglycidyl ethers of a dihydric phenol with one or more dihydric phenols having the amido or hydroxymethyl substituents under conditions sufficient to cause the hydroxyl moieties to react with epoxy moieties to form a polymer backbone having ether linkages and pendant hydroxyl moieties and amido and/or hydroxymethyl moieties. Conditions conventionally employed in the reaction of diglycidyl ethers with phenols to form ether linkages are suitably employed in preparing the resins of this invention. Examples of such suitable conditions are set forth in U.S. Pat. No. 4,647,648, which is hereby incorporated by reference in its entirety. In general, however, the process for preparing the polymers is carried out so that the unreacted epoxy groups in the finished polyether are minimized. By minimizing the epoxy groups in the polyether, the essential thermoplastic character of the polyether can be retained. Preferred conditions for preparing such resins are set forth in the following working examples.

The diglycidyl ethers of the dihydric phenols are preferably the diglycidyl ethers of bisphenol ketone (sometimes called bisphenol K), bisphenol sulfone, resorcinol, hydroquinone, 4,4'-isopropylidene bisphenol (bisphenol A), 4,4'-dihydroxydiphenylethylmethane, 3,3'-dihydroxydiphenyldiethylmethane, 3,4'-dihydroxydiphenylmethylpropylmethane, bisphenol, 4,4'-dihydroxydiphenyloxide, 4,4'-dihydroxydiphenylcyanomethane, 4,4'-dihydroxybiphenyl, 4,4'-dihydroxybenzophenone, 4,4'-dihydroxydiphenyl sulfide, 4,4'-dihydroxydiphenyl sulfone, 2,6-dihydroxynaphthalene, 1,4'-dihydroxynaphthalene, catechol and other dihydric phenols listed in U.S. Pat. Nos. 3,395,118; 4,438,254 and 4,480,082 which are hereby incorporated by reference as well as mixtures of one or more of such diglycidyl ethers. Of these preferred diglycidyl ethers, those of biphenol and resorcinol are more preferred, with the diglycidyl ether of resorcinol being most preferred.

Examples of preferred dihydric phenols having amido, N-substituted amido and/or hydroxymethyl substituents include 2,2-bis(4-hydroxyphenyl)acetamide, 2,2-bis(4-hydroxyphenyl)ethanol, 2,2-bis(4-hydroxyphenyl)-N-methylacetamide, 2,2-bis(4-hydroxyphenyl)-N-ethylacetamide, 2,2-bis(4-hydroxyphenyl)-N-propylacetamide, 2,2-bis(4-hydroxyphenyl)-N,N-dimethylacetamide, 2,2-bis(4-hydroxyphenyl)-N-methyl-N-ethylacetamide, 3,5-dihydroxybenzamide, 2,4-dihydroxybenzamide, 2,4-dihydroxy-1-[N-(2-hydroxyethyl)]benzamide, and 2,4-dihydroxy-1-[N-(2-hydroxypropyl)]benzamide. Of these preferred dihydric phenols, 3,5-dihydroxybenzamide and 2,2-bis(4-hydroxyphenyl)acetamide are most preferred.

Alternatively, the copolyether can be suitably prepared by contacting one or more diglycidyl ethers of the dihydric phenol having the amido, N-substituted amido and/or hydroxymethyl substituents with one or more of the other dihydric phenols previously listed herein as suitable using the procedures and conditions of U.S. Pat. No. 4,647,648.

For the purposes of this invention, the term "barrier polymer" means that the polymer exhibits an oxygen transmission rate which is less than 5, preferably less than 2, most preferably less than 1, cubic centimeters-mil/100 inch$^2$-atmosphere-day.

The barrier articles, e.g., containers, films and coatings, of this invention are fabricated from the copolyethers using conventional fabricating techniques for normally solid, thermoplastic polymers such as extrusion, compression molding, injection molding, blow molding and similar fabrication techniques commonly employed to produce such articles.

ILLUSTRATIVE EMBODIMENTS

The following examples are given to illustrate the invention and should not be interpreted as limiting it in any way. Unless stated otherwise, all parts and percentages are given by weight.

EXAMPLE 1

A. Preparation of 2,2-Bis(4-hydroxyphenyl)acetamide

In a 3000-mL flask, a stirred mixture of 155.6 g (0.55 mole) of potassium 2,2-bis(4-hydroxyphenyl)acetate and 1.5 L of tetrahydrofuran (distilled from calcium hydride) is maintained at 10° C. and 48 mL (0.54 mole) of oxalyl chloride is added dropwise via an addition funnel over a period of 3 hours. The mixture is allowed to warm to 25° C. while stirring the mixture another 66 hours. The mixture is then added over a period of 3.5 hours to 750 mL of aqueous ammonia (11 moles of NH$_4$OH) at 10° C. The tetrahydrofuran is removed and the residual product is mixed with 1 L of methyl isobutyl ketone (MIBK) and then acidified with aqueous HCl (10 percent). The resulting white solid is removed by filtration, and the organic layer is separated and extracted with aqueous NaHCO$_3$ (10 percent). The aqueous layer is washed with MIBK (2×50 mL) and the combined organic phase concentrated in vacuo to yield 89.9 g of a brown oil. The desired amide is recovered from the brown oil by recrystallization from an ethyl acetate/THF mixture to yield 50.9 g (38 percent yield) of a tan solid. Analysis of the tan solid by proton NMR and carbon NMR indicates it to be 2,2-bis(4-hydroxyphenyl)acetamide.

B. Preparation of the Copolyether

In a 100-mL flask, a mechanically stirred mixture of 4.87 g (20.0 mmol) of the dihydric phenyl acetamide of Part A, 6.98 g (20.4 mmol) of the diglycidyl ether of bisphenol A and 8 mL of phenoxypropanol is heated under nitrogen to a temperature of 140° C. A 0.5-mL portion of ethyltriphenylphosphonium acetate (70 percent in methanol) is added, and the temperature of the mixture immediately rises to about 145° C. To insure effective stirring of the increasingly viscous solution, an additional 8 mL of phenoxypropanol is added over a period of 35 minutes while the temperature of the solution is maintained at about 150° C. The solution is allowed to cool to 120° C. and is then diluted with dimethylformamide (DMF) to a total volume of 75 mL. The resulting solution is poured slowly into a vigorously stirred blender containing 400 mL of a 3:1 mixture of methanol and water to precipitate fibrous solid. This solid is then washed with 400 mL of methanol and 400 mL of water in a high speed blender. The resulting white granular polymer is collected via filtration, air dried, then redissolved in DMF and precipitated a second time. The polymer is collected via filtration and then air dried in vacuo at 80° C. for 24 hours to yield 10.7 g (90 percent of theoretical yield) of a copolyether represented by the formula:

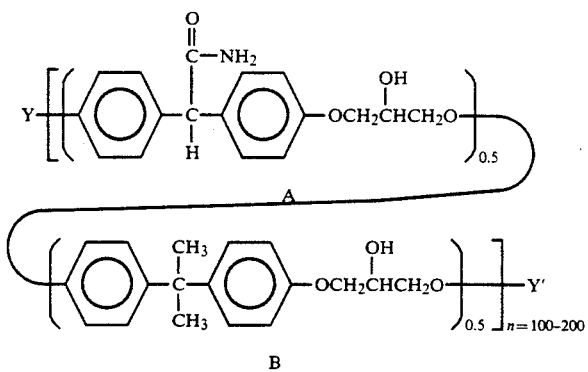

wherein Y and Y' are as previously defined.

C. Copolyether Testing

The copolyether is tested for intrinsic viscosity and Tg. Copolyether specimens (10 cm × 10 cm × 0.013 cm) for oxygen barrier evaluations are prepared by compression molding samples (3.5 g) of the polymer of Part B between Teflon sheets in a brass template at 200° C.-230° C. at 2000 psi (13.8 mPa) for 10-30 minutes, then at 200,000-400,000 psi (1380-2750 mPa) for 2-4 minutes and then cooled at 200,000-400,000 psi for 10 minutes. Oxygen transmission rates are then measured for the samples. The results of these tests (Sample No. 1a) are reported in Table I.

D. Additional Copolyethers

For purposes of further exemplification, several additional 1:1 copolyethers of 2,2-bis(4-hydroxyphenyl)acetamide and other dihydric phenols listed in Table I are similarly prepared and tested, and the results of such tests (Sample Nos. 1b-1c) are reported in Table I.

EXAMPLE 2

A. Preparation of 2,2-Bi-(4-hydroxyphenyl)ethanol

To a 2-liter Morton flask equipped with a mechanical stirrer and a half-moon paddle is charged 30.50 g (0.125 mole) of 2,2-bis(4-hydroxyphenyl)acetic acid and 1 L of tetrahydrofuran (THF) under a nitrogen atmosphere. $LiAlH_4$ (18.9 g, 0.5 mole) is added with stirring to the reaction mixture over a period of six days. The reaction temperature is about 25° C. at the outset and is increased to 65° C. after one day and maintained at that temperature throughout the remaining five days of the addition of the $LiAlH_4$. After a total of 12.5 days, the reaction mixture is cooled to 0° C. and 100 mL of water is added dropwise to the reaction mixture. The pH of reaction mixture is lowered to a pH of 1 by the addition of 10 percent HCl and the resulting phases are separated. The organic phase is evaporated to form a solid and the solid is dissolved in 500 mL of methyl isobutyl ketone. After washing the resulting solution with 100 mL of an aqueous solution of 5 percent $NaHCO_3$, the solution is concentrated in vacuo to yield 30.7 g of 2,2-bis(4-hydroxyphenyl)ethanol as an orange gum. This gum is recrystallized from 430 mL of water to yield 23.0 g of a light brown solid. Upon vacuum drying at 100° C., the solid melted and lost weight to 21.1 g (yield of 73 percent) which weight loss corresponds to one molar equivalent of water.

Following the procedure of Part B of Example 1 except that 2,2-bis(4-hydroxyphenyl)ethanol is allowed to react with the diglycidyl ethers of bisphenol A, biphenol and resorcinol. Several copolyethers are prepared and then tested in accordance with Part C of Example 1. The results of these tests (Sample Nos. 2a-2c) are also reported in Table I.

EXAMPLE 3

Following the procedure of Part B of Example 1 except that different dihydric phenyl amides as listed in Table I are substituted for 2,2-bis(4-hydroxyphenyl)acetamide, several copolyethers are prepared and then tested in accordance with Part C of Example 1. The results of these tests (Sample Nos. 3a-3d) are also reported in Table I.

EXAMPLE 4

A. 2,2-Bis(4-hydroxyphenyl)acetamide Diglycidyl Ether

Benzyltrimethylammonium chloride (0.10 g, 0.54 mmole), 2,2-bis(4-hydroxyphenyl)acetamide (48.65 g, 0.2 mole), and epichlorohydrin (400 mL, 5.10 moles) are added to a one-liter three-necked round bottom flask equipped with a water-cooled condenser, an overhead mechanical stirrer, and a thermometer with an attached temperature controller. The stirred reaction mixture is heated to 82° C. under nitrogen for 44 hours and then cooled to 30° C. Aqueous NaOH (48 g of 50 percent soln, 0.6 mole) is added dropwise with stirring over a 30-minute period, the mixture is stirred for 24 hours and another 8.0 g (0.1 mole) of 50% NaOH is added. After stirring for 18 hours, the reaction mixture is poured into one liter of methylene chloride, washed with two portions (one liter each) of water, and the organic fraction is dried over magnesium sulfate. Solvent is removed under reduced pressure to yield an amber-colored oil which crystallizes on standing. This crude product is then recrystallized twice from toluene and dried in vacuo at 50° C. for 16 hours to yield 37.0 g (52 percent) of the aforementioned diglycidyl ether.

B. Preparation of Poly(amide ether)

The diglycidyl ether of Part A (11.37 g, 61.19 meq epoxide), N,N'-bis(3-hydroxyphenyl)adipamide (9.85 g, 30.0 mmol, 60.0 meq phenolic hydroxyl), and 13 mL of phenoxypropanol are added to a 100-mL reactor equipped with a thermometer, overhead mechanical stirrer, and a nitrogen sparge. The mixture is heated to 140° C. and 0.75 mL of ethyl-triphenylphosphonium acetate (70 percent in methanol) is added, and the temperature of the mixture immediately rises to about 150° C. To insure effective stirring of the increasingly viscous solution, an additional 10 mL of phenoxypropanol is added in 2-mL portions over a period of 20 minutes while the temperature of the solution is maintained at about 155° C.–160° C. The solution is allowed to cool to 120° C. and is then diluted with dimethylformamide (DMF) to a total volume of 100 mL. The resulting solution is poured slowly into a vigorously stirred blender containing 400 mL of a 3:1 mixture of methanol and water to precipitate fibrous solid. This solid is then washed with 400 mL of methanol and 400 mL of water in a high speed blender. The resulting white granular polymer is collected via filtration, air dried, and then redissolved in DMF and dried in vacuo at 80° C. for 24 hours to yield 16.9 g (80 percent of theoretical yield) of a copolyether represented by the formula:

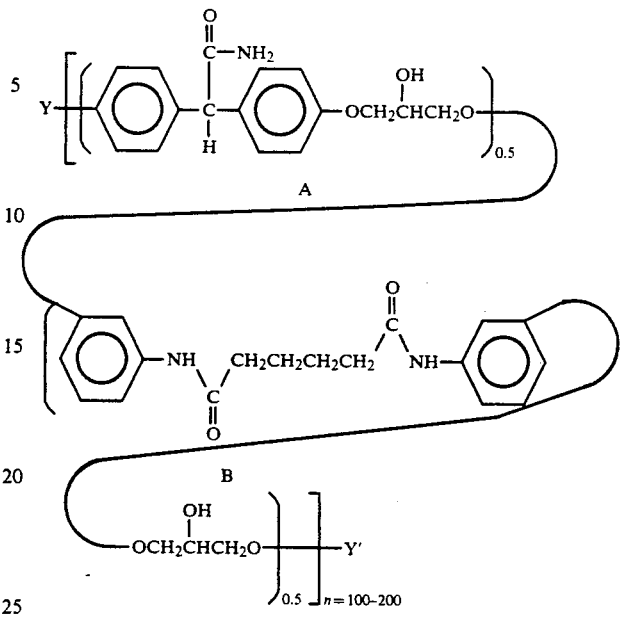

The copolyether is tested for barrier to oxygen and the results of the test (Sample No. 4) are reported in Table I.

TABLE I

| Sample No. | Composition A | Composition B | A/B Ratio | n inh[1] (dL/g) | $T_g$[2] (°C.) | OTR[3],[4] 75–95% RH[5] |
|---|---|---|---|---|---|---|
| 1a | ⌬-C(H)(C(O)NH₂)-⌬ | ⌬-C(CH₃)₂-⌬ | 0.5:0.5 | 0.55 | 128 | 1.23 |
| 1b | ⌬-C(H)(C(O)NH₂)-⌬ | ⌬-⌬ | 0.5:0.5 | 0.52 | 111 | 0.43 |
| 1c | ⌬-C(H)(C(O)NH₂)-⌬ | m-xylylene | 0.5:0.5 | 0.43 | 95 | 0.12 |
| 2a | ⌬-C(H)(CH₂OH)-⌬ | ⌬-C(CH₃)₂-⌬ | 0.5:0.5 | 0.57 | 100 | 1.59 |
| 2b | ⌬-C(H)(CH₂OH)-⌬ | ⌬-⌬ | 0.5:0.5 | 0.59 | 92 | 0.62 |
| 2c | ⌬-C(H)(CH₂OH)-⌬ | m-xylylene | 0.5:0.5 | 0.77 | 57 | 0.72 |

TABLE I-continued

| Sample No. | Composition A | Composition B | A/B Ratio | n inh[1] (dL/g) | Tg[2] (°C.) | OTR[3],[4] 75-95% RH[5] |
|---|---|---|---|---|---|---|
| 3a | (3,5-dimethylphenyl)-CH(C(=O)NHCH₃)- | bisphenol A | 0.5:0.5 | 0.26 | 98 | 2.60 |
| 3b | (3,5-dimethylphenyl)-CH(C(=O)N(CH₃)₂)- | bisphenol A | 0.5:0.5 | 0.74 | 99 | 3.52 |
| 3c | 3,5-dimethylbenzamide | bisphenol A | 0.5:0.5 | 0.33 | 84 | 0.52 |
| 3d | 3,5-dimethyl-N-(2-hydroxyethyl)benzamide | bisphenol A | 0.5:0.5 | 0.61 | 112 | 1.08 |
| 3e | 3,5-dimethyl-N-(2-hydroxyethyl)benzamide | phenol | 0.5:0.5 | 0.47 | 73 | 0.51 |
| 4 | bis(tolyl)CH-C(=O)NH₂ with adipamide bis(tolyl) co-monomer | — | 0.5:0.5 | 0.35 | 122 | 0.18 (60–80% RH) |
| C* | none | bisphenol A | 0:1 | 0.44 | 102 | 9.0 |

[1] η inh — inherent viscosity in DMF at 0.5 g/dL and 25° C.
[2] Tg — glass transition temperature
[3] ASTM Method D-3985 measured for compression molded films (23° C.–24° C.)
[4] Oxygen transmission rate (OTR) measured in cm³-mil/100 in²-atm-day
[5] Relative humidity of the oxygen stream
*Not an example of the invention As evidenced by comparing the Oxygen Transmission Rates (OTR) for Sample Nos. 1a, 2a, and 3a–3d with the OTR for Sample No. C, the inclusion of the monomer (A) produces a surprisingly large reduction in the oxygen permeability of the polyether.

What is claimed is:

1. A diglycidyl ether of an amido-dihydric phenol selected from the group consisting of 2,2-bis(4-hydroxyphenyl)acetamide and 2,4-dihydroxybenzamide.

2. A diglycidyl ether of an N-substituted amidodihydric phenol selected from the group consisting of 2,2-bis(4-hydroxyphenyl)-N-methylacetamide, 2,2-bis(4-hydroxyphenyl)-N-ethylacetamide, 2,2-bis(4-hydroxyphenyl)-N-propyl-acetamide, 2,2-bis(4-hydroxyphenyl)-N,N-dimethylacetamide, 2,2-bis(4-hydroxyphenyl)-N-methyl-N-ethylacetamide, 2,4-dihydroxy-1-[N-(2-hydroxyethyl)]benzamide, and 2,4-dihydroxy-1-[N-(2-hydroxypropyl)]benzamide.

* * * * *